United States Patent [19]

Lind

[11] 4,002,165

[45] Jan. 11, 1977

[54] AUTO-TRACTION TABLE

[76] Inventor: Gertrud Agnes Matilda Lind, Grev Turegatan 22, 114 38 Stockholm, Sweden

[22] Filed: May 7, 1975

[21] Appl. No.: 575,214

[52] U.S. Cl. .......... 128/71

[51] Int. Cl.[2] .......... A61F 5/00

[58] Field of Search .......... 128/71–74, 128/68.1, 84

[56] References Cited

UNITED STATES PATENTS

| | | | |
|---|---|---|---|
| 2,088,747 | 8/1937 | Kelley | 128/84 |
| 2,232,952 | 2/1941 | Longfellow | 128/84 |
| 2,640,480 | 6/1953 | Hill | 128/71 X |
| 3,388,700 | 6/1968 | Mountz | 128/71 X |

FOREIGN PATENTS OR APPLICATIONS

| | | | |
|---|---|---|---|
| 1,020,154 | 11/1957 | Germany | 128/71 |

*Primary Examiner*—Lawrence W. Trapp
*Attorney, Agent, or Firm*—Young & Thompson

[57] ABSTRACT

A traction table has a top for a patient to lie on and a flexible device for encircling a portion of the patient's body. Spaced above the foot end of the table is a horizontal bar, supported by a pipe frame, on which the patient can press with the feet. At the head end of the table, another pipe frame comprises at least two vertical pipes on each side of the longitudinal midline of the table, as supports for the patient's hands. A holder is horizontally and vertically adjustably secured to the pipes at one of the two ends of the table, and a longitudinally adjustable traction strap interconnects that holder with the flexible device. The traction strap includes a dynamometer to measure the traction force and to permit the patient to exert a predetermined force by pushing or pulling against the respective frames.

15 Claims, 6 Drawing Figures

AUTO-TRACTION TABLE

The present invention relates to an auto-traction table.

This table is used in the treatment of pain in the spin. In contrast to the other traction tables the auto-traction table permits smooth and continuous adjustment of the traction force and of its direction in relation to the region being treated. By this means it is easy to avoid overloading and incorrect application of traction. With this new table the correct traction force is determined by the patient's own muscular power and is therefore referred to as an auto-traction table.

An embodiment of a traction table according to the present invention is shown in the accompanying drawings, in which.

Figure 1:
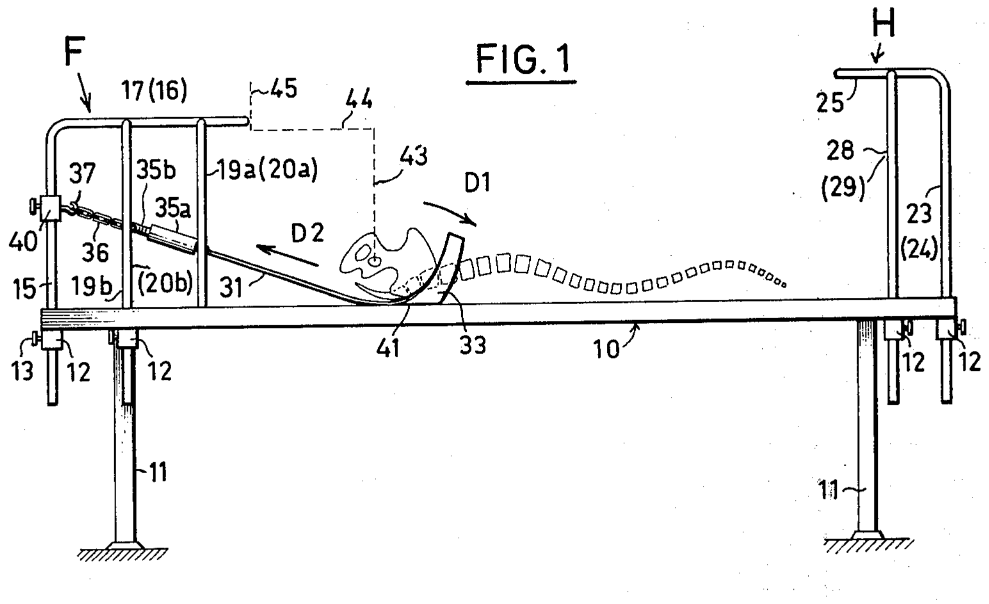
FIG. 1 is a schematic lateral view of the traction table with a non-adjustable top on which a spinal column with its pelvis is placed in order to illustrate the distribution of forces.

The traction table shown in FIG. 1 consists of the table-top itself 10 resting on a floor stand having four legs, 11. Rigid pipe frames, H at the head-end and F at the foot-end, are attached to the ends of the table. The table is upholstered to form a comfortable supporting surface for the patient.

Figure 2:
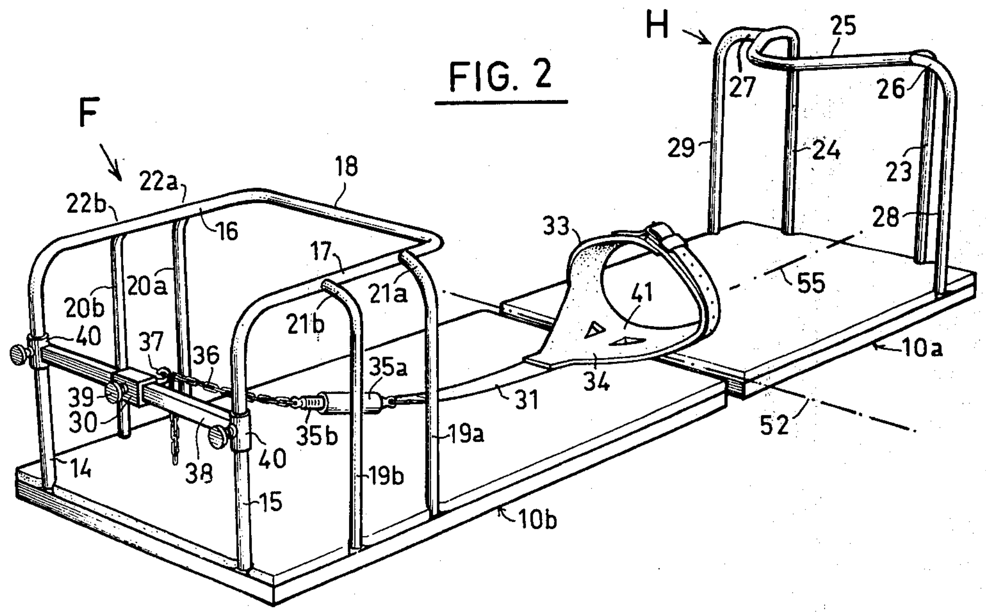
FIG. 2 is a schematic view of the traction table with a top consisting of two parts which may be angularly adjusted in relation to each other.

The construction of frames H and F is seen better in FIG. 2. The table differs from that shown in FIG. 1 mainly in the top in FIG. 2 consists of two parts, 10*a*, 10*b*. Both of them are supported by frames 10*c*, 10*d* in FIG. 3, which may be adjusted to various angles as indicated by the arrows 10*e*, 10*f*, 10*g* in FIG. 3.

In FIG. 1 frames H and F are supported by sleeves 12, with locking screws 13, which permit them to be raised or lowered.

Frames H and F, shown in FIG. 2, can likewise be raised or lowered, but for the sake of simplicity they are shown rigidly attached. From FIGS. 1 and 2 it is evident that frame F at the foot-end of the table includes two vertical pipes 14, 15 at a distance from each other shorter than the width of the table. The upper parts of the se pipes extend into two parallel and horizontal pipes 16, 17, located at the table and having their front ends connected by a transverse pipe, 18, intended to serve as a support for the patient's feet, as schematically indicated in FIG. 1. As frame F is adjustable, the height of the transverse pipes above the table can be adjusted to the length of the patient's legs, the thighs being at approximately right angles to the table and the lower part of the legs horizontal.

These 90° angles of the hip and knee joints leads to a decrease in the lordosis and results in a traction force of maximum effect when at right angles to the surface of the disk.

Frame F has another four vertical pipes 19*a*, 19*b* and 20*a*, 20*b*, which are attached to the sides of the table and are connected to pipes 16, 17 through horizontal pipes 21*a*, 21*b* and 22*a*, 22*b*. Pipes 18, 19*a* 19*b*, 20*a*, 20*b* and 21*a*, 21*b*, 22*a*, 22*b* form a frame which presents a great number of places against which the patient may press his feet in various alternative combinations of positions.

Frame H at the head-end of the traction table includes two vertical pipes 23, 24. At their upper ends, pipes 23, 24 extend into a V-shaped bow, 25, which is located above the table. This bow can be grasped by the patient or leaned on by the physician to afford a support for his body. To the legs of the V-bow 25 are secured two horizontal pipe sections, 26, 27, which form an extension of the upper ends of the two vertical side pipes, 28, 29, which are attached near the edges of the table. Pipes 23, 28, 24, 29 and 26, 27 present a number of places for the patient to get a firm grip with his hands and thus allow alternative combinations.

The table-top may have a detachable section which can be replaced by another section which permits roentgenograms to be taken to check traction in order to ascertain the correcting effect. This section can also be replaced in order to make it easy to provide the patient with a bed pan.

To carry out traction treatment, a holder, 30, for securing the traction strap is mounted on either frame H or F, FIGS. 1 and 2 show traction strap 31 secured to frame F. A belt 33 may be secured around the waist and forms a truncated cone (see FIGS. 1,2) when the belt is closed to ensure it rests firmly on the patient's hips. The base of the cone faces the stand to which the traction strap has been fastened. There is a projecting supporting flap 34 in the middle of the belt. One end of traction strap 31 is fastened to the upper side of this flap while its other end is fastened to one end of a dynamometer 35*a*. The spring of the dynamometer affords an elasticity suitable for auto-traction. The dynamometer is of a well known construction and consists of a sleeve 35*a* and a plunger 35*b* equipped with a graded scale.

To the other end of the dynamometer, i.e. the plunger, is secured one end of a chain 36, the other end of which is fastened to a hook 37 on the sleeve 30. The sleeve is mounted on a transverse bar 38 and, in the example shown, it may be moved along the bar and locked in different positions by means of a locking screw 39. The ends of the bar 38 at the foot-end (or head-end) are secured to sleeves 40, which may be moved along a vertical pipes 14, 15 and 23, 24, respectively, and locked in different positions by means of locking screws. Thus, the treatment of the thoracic or lumbar spine can be adjusted by moving the rear end of the traction strap to any desired position in a vertical as well as in a horizontal direction.

Figure 3:
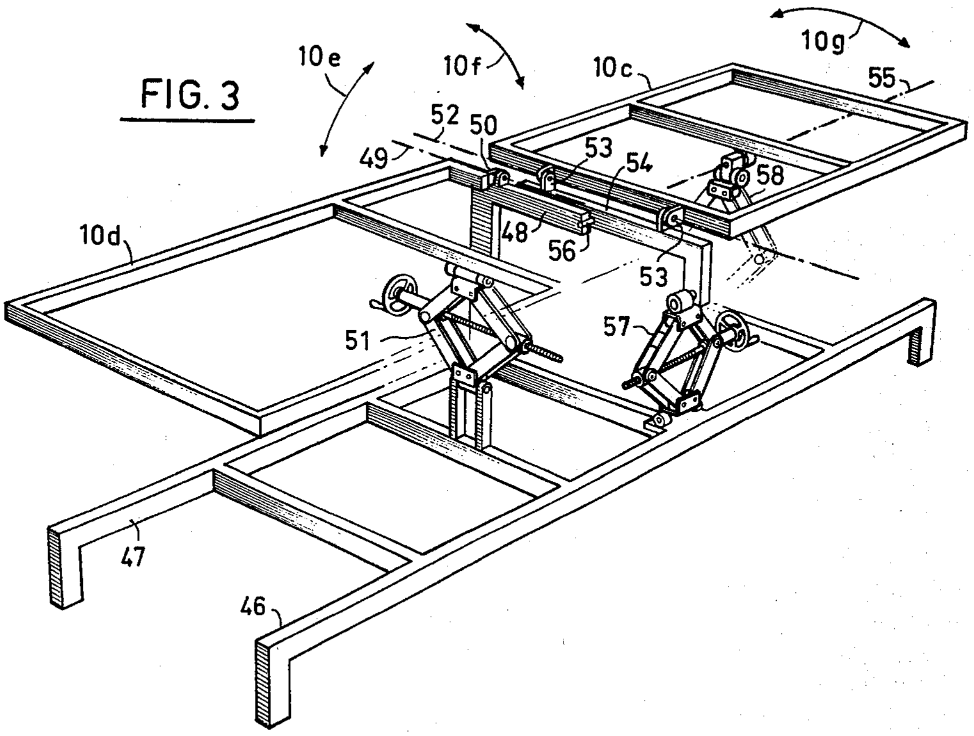
FIG. 3 is a schematic view of two frames supporting the two parts of the table-top in FIG. 2.
Figure 5:
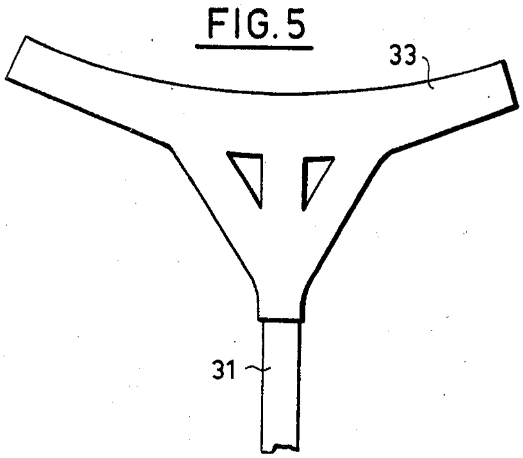
FIG. 5 is a view of the flexible device open.
Figure 6:
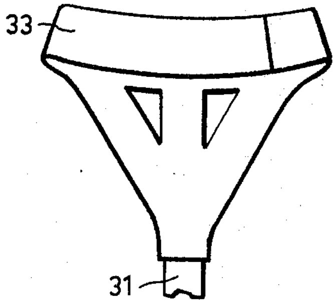
FIG. 6 is a view of the flexible device closed.

Although the rigid traction table shown in FIG. 1 allows of a great number of different points of application and directions of the auto-traction force, it may be more convenient to use the two-part traction table in FIGS. 2 and 3 with one part 10*a* and 10*c* adjustable angularly in two planes around the longitudinal and transverse axes and the other part 10*b* and 10*d* adjustable in one plane, around the transverse axis.

As it is possible to vary the position of the rear attachment point of the traction strap, both horizontally and vertically, this combined with the possibilities just mentioned, makes possibilities just mentioned, makes possible any desired adjustment of the traction direction.

The frame in FIG. 3 consists of two parallel legs 46, 47 with cross bars and a U-shaped frame 48. These support frame 10*d*, corresponding to 10*b*, which is provided with projecting lugs 50 mounted on frame 48 topivot frame 10*d* about a transverse axis 49. Frame 10*d* may be angularly adjusted by means of a mechanical jack 51, which is only schematically indicated in FIG. 3.

The other frame 10*c*, corresponding to 10*a*, van be moved by means of jacks around a transverse axis 52 and around a longitudinal axis 55 to any desired angular position.

Figure 4:
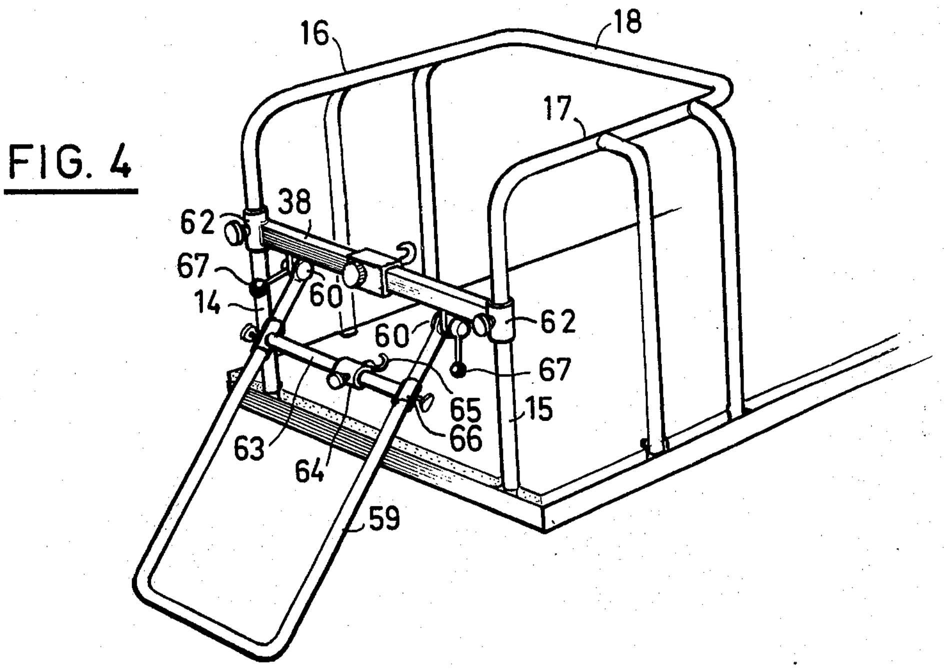
FIG. 4 is a view of one end of the traction table shown in FIG. 1 with an attachment for patients who lack sufficient muscular power.

FIG. 4 schematically illustrates an additional detachable device which can be mounted at the foot-end of the table. This device consists of a U-shaped member 59 having its ends lockably hinged at 60 to cross-bar 38. This member 59 may be swung to any desired position and locked by means of the handles 67 shown. Between the legs of th U-shaped member is a sliding bar 63, which at its end has sleeve 66, lockable on the legs. A sleeve 64 can be moved along bar 63 and locked in any desired position. Sleeve 64 has a hook 65, on which a chain 36 in FIGS. 1 and 2 can be fastened. If the patient is too weak for auto-traction, he may grip the vertical pipes at the head-end with his hands so that the person giving the treatment may regulate the member 59. Traction is produced when bar 63 is moved along sleeve 64 of the U-shaped member 59 as well as when sleeve 64 is moved sideways. Although not shown the pivots 67 of the legs of the U-shaped member 59 are provided with locking teeth which can lock the device in any position.

Pipe frames H and F are so constructed that they may advantageously be used as supports during gymnastic exercises carried out as rehabilitation to strengthen the muscles of the patient.

As the whole table is very light it is easily moved when it is on wheels. These wheels can be locked.

What is claimed is:

1. A traction table having a head and a foot and a top for a patient to lie on and a flexible arrangement that can be fastened around a part of the body such as the waist or the head of the patient lying on the table and a traction strap secured to a holder fastened at one end of the table, a pipe frame at the head (H) and at the foot (F) of the table, said frame at the foot comprising a transverse pipe (18) spaced above the tabletop (10, 10*a* and 10*b*) to provide a foot stop for the patient lying supine with the legs raised and flexed, the frame at the head end having at least two vertical pipes (28, 29, 23, 24) on each side of the longitudinal midline of the table as supports for the patient's hands, at least one of said pipes having a vertically adjustable holder (30) for securing a longitudinally adjustable traction strap (31), which comprises a dynamometer (35, 35*a* and 35*b*) which measures the traction force and gives the traction strap suitable elasticity for auto-treatment, whereby the patient can choose the traction force he himself produces by his own muscular exertion when pulling and pressing against the respective pipe frames.

2. Table according to claim 1, characterised by the fact that the traction belt (31) is integrally connected with the flexible arrangement (33) at a certain point (41) on the latter so that the point at which the pull is applied on the circumference of the part of the body can be adjusted by pulling the flexible arrangement round the part of the body in question until the fastening point is in desired position.

3. Table according to claim 1, characterised by the fact that the frame has at said foot end two vertical pipes (14 and 15) situated at the end of the table and at a distance behind a transverse bar (38) which is adjustable and can be locked in desired position on the vertical pipes carrying the holder (30) for securing the traction strap.

4. Table according to claim 3, characterised by the fact that the holder (30) can be adjusted along the transverse bar (38) and be locked in desired position.

5. Table according to claim 1, characterised by the fact that one end of the traction strap is fastened to a belt to be fastened above the upper part of the hips (iliac crest), while the other end of the strap is secured to one of the ends of said dynamometer which is a spring dynamometer (33), the spring of which is situated in the longitudinal direction of the strap, the end of which is in turn attachable via a chain to a hook (37) on the vertically adjustable holder.

6. Table according to claim 1 with a belt that can be fastened round a patient's waist, characterised by the fact that the belt (33) when laid out flat, is curved so that when fastened round the patient's waist, it forms a truncated cone, whose wide end faces the foot end of the table, so that when fitted the belt snugly fits the upper part of the patient's hips.

7. Table according to claim 6, characterised by the fact that at the site of attachment to the traction strap the belt has a wider portion in the form of a flap (34) that extends over the traction strap to form a comfortable supporting surface for the patient, especially when he is supine.

8. Table according to claim 1 characterised by the fact that the pipe frame at the foot of the table is symmetrical on either side of the vertical midplane of the table and comprises two posterior vertical pipes (14, 15) situated at the end of the table and separated by a distance smaller than the width of the table and two vertical anterior side pipes (19, 20) situated near the side edges of the table and at a distance from the posterior pipes, the upper ends of the posterior pipes merging with two substantially parallel pipes (16, 17), parallel to the table top, whose anterior ends merge with a transverse pipe (18) serving as a foot support, while the side pipes 19 and 20 are bent at the level of the parallel pipes to form pipes 21 and 22 forming the foot support and joining the parallel pipes substantially perpendicularly and at a distance behind the transverse pipe serving as a foot support.

9. Table according to claim 1 characterised by the fact that the pipe frame, at the head of the table, is symmetric on either side of the vertical midplane of the table and comprises two vertical tubes (23 and 24) situated at the end of the table and separated by a distance smaller than the width of the table and two vertical pipes (28 and 29) situated opposite one another almost at the end of the table and that the upper ends of the pipes situated at the end of the table merge with two substantially parallel shanks of a U-shaped member (25), which extends over the table and forms both a hand grip for the patient or an abdominal or thoracic support for the person supervising the treatment and occasionally having to lean over the patient at the head end to place the patient in proper position and that the vertical side pipes (28, 29) form a hand support for the patient and that at the level of the U-member the upper ends are bent to form pipe segments 26 and 27, which provides alternative hand supports and are fastened to the shanks of the U-shaped member.

10. Table according to claim 8, characterised by the fact that the two vertical bars at either of the table support a detachable cross bar (60) on which are pivoted the ends of a U member to whose shanks is fastened a transverse pull-pipe (59*a*) that serves alternately as a hand support or a carrier for a traction belt holder, so that the person supervising the treatment can grip the lower end of this stirrup and use it as a lever for rotating the pull pipe when the patient is not strong enough to do auto-traction.

11. Table according to claim 1, characterised by the fact that at least the pipe frame at the foot of the table can be raised and lowered relative to the top of the table to permit adjustment of the transverse foot stop to desired height above the level of the top of the table.

12. Table according to claim 1, characterised by the fact tht it consists of two parts (10*a*, 10*b*), the angle between them being adjustable by rotation about transverse axles (49, 52).

13. Table according to claim 12, characterised by the fact that at least that part of the table at the head end is also angularly adjustable by rotation about a longitudinal axis in the midplane of the table.

14. Table according to claim 13, characterised by the fact that the floor support of the table has two frames, (10*c*, 10*d*) each supporting a part of the table and at those ends facing each other are rotatable about transverse axes (49, 52), that at least the transverse axis for the frame supporting the head end of the table is rotatable about a longitudinal axis 56 in the midplane of the table and that continuously adjustable arrangements (51, 57, 58), are provided for angular adjustment of both frames by rotation about the above-mentioned axes.

15. Table according to claim 1, the top of the table being in a plurality of sections, and means to adjust the angle of said sections relative to each other.

* * * * *